United States Patent
Zilbershtein et al.

(10) Patent No.: US 10,508,065 B2
(45) Date of Patent: Dec. 17, 2019

(54) METHODS OF PREPARING OLIGOMERS OF AN OLEFIN

(71) Applicant: PUBLIC JOINT STOCK COMPANY "SIBUR HOLDING", Tobolsk (RU)

(72) Inventors: Timur Mikhailovich Zilbershtein, Kazan (RU); Denis Alekseevich Lenev, Khimki (RU); Maxim Vladimirovich Lipskikh, Tomsk (RU)

(73) Assignee: PUBLIC JOINT STOCK COMPANY "SIBUR HOLDING", Tobolsk (RU)

( * ) Notice: Subject to any disclaimer, the term of this patent is extended or adjusted under 35 U.S.C. 154(b) by 0 days.

(21) Appl. No.: 15/539,135

(22) PCT Filed: Dec. 23, 2014

(86) PCT No.: PCT/RU2014/000973
§ 371 (c)(1),
(2) Date: Jun. 22, 2017

(87) PCT Pub. No.: WO2016/105227
PCT Pub. Date: Jun. 30, 2016

(65) Prior Publication Data
US 2017/0369391 A1 Dec. 28, 2017

(51) Int. Cl.
*C07C 2/30* (2006.01)
*C07C 2/08* (2006.01)
(Continued)

(52) U.S. Cl.
CPC .............. *C07C 2/30* (2013.01); *C07C 11/02* (2013.01); *C07C 11/107* (2013.01); *C08F 110/02* (2013.01); *C08F 2500/02* (2013.01)

(58) Field of Classification Search
CPC .......... B01J 2231/12; C07C 2/08; C07C 2/24; C07C 2/30
(Continued)

(56) References Cited

U.S. PATENT DOCUMENTS

| 6,455,648 B1 | 9/2002 | Freeman et al. |
| 8,252,955 B2 | 8/2012 | Gao et al. |

(Continued)

FOREIGN PATENT DOCUMENTS

| EP | 0 780 353 | 6/1997 |
| EP | 2 529 832 | 12/2012 |

(Continued)

OTHER PUBLICATIONS

International Search Report and Written Opinion dated Sep. 18, 2015, directed to International Application No. PCT/RU2014/000973; 9 pages.
(Continued)

*Primary Examiner* — Youngsul Jeong
(74) *Attorney, Agent, or Firm* — Morrison & Foerster LLP

(57) ABSTRACT

Methods of preparing oligomers of an olefin are provided. The methods can include providing an alkylaluminum compound and irradiating the alkylaluminum compound with microwave radiation to provide an irradiated alkylaluminum compound. The methods can further include mixing the irradiated alkylaluminum compound with a chromium compound, a pyrrole compound, and a zinc compound to provide a catalyst composition. The methods can further include contacting an olefin with the composition to form oligomers of the olefin. The olefin can include ethylene, and the oligomers of the olefin can include 1-hexene.

9 Claims, 1 Drawing Sheet

(51) Int. Cl.
*C07C 11/02* (2006.01)
*C08F 110/02* (2006.01)
*C07C 11/107* (2006.01)

(58) Field of Classification Search
USPC .................................. 526/161; 585/502, 512
See application file for complete search history.

(56) References Cited

U.S. PATENT DOCUMENTS

| | | | |
|---|---|---|---|
| 8,252,956 B2 | 8/2012 | Gao et al. | |
| 2005/0131262 A1* | 6/2005 | Dixon | B01J 31/1805 585/511 |
| 2011/0282016 A1* | 11/2011 | Carter | C07C 2/36 526/145 |
| 2012/0302715 A1* | 11/2012 | Zilbershtein | B01J 31/143 526/348.5 |

FOREIGN PATENT DOCUMENTS

| | | |
|---|---|---|
| WO | WO-99/19280 | 4/1999 |
| WO | WO-2011/140629 | 11/2011 |
| WO | WO-2016/105226 | 6/2016 |
| WO | WO-2016/105228 | 6/2016 |

OTHER PUBLICATIONS

Yang, Y. et al. (2000). "Roles of chloro compound in homogeneous [Cr(2-ethylhexanoate)$_3$/2,5-dimethylpyrrole/triethylaluminum/chlorocompound] catalyst system for ethylene trimerization," *Applied Catalysis A: General* 193: 29-38.

* cited by examiner

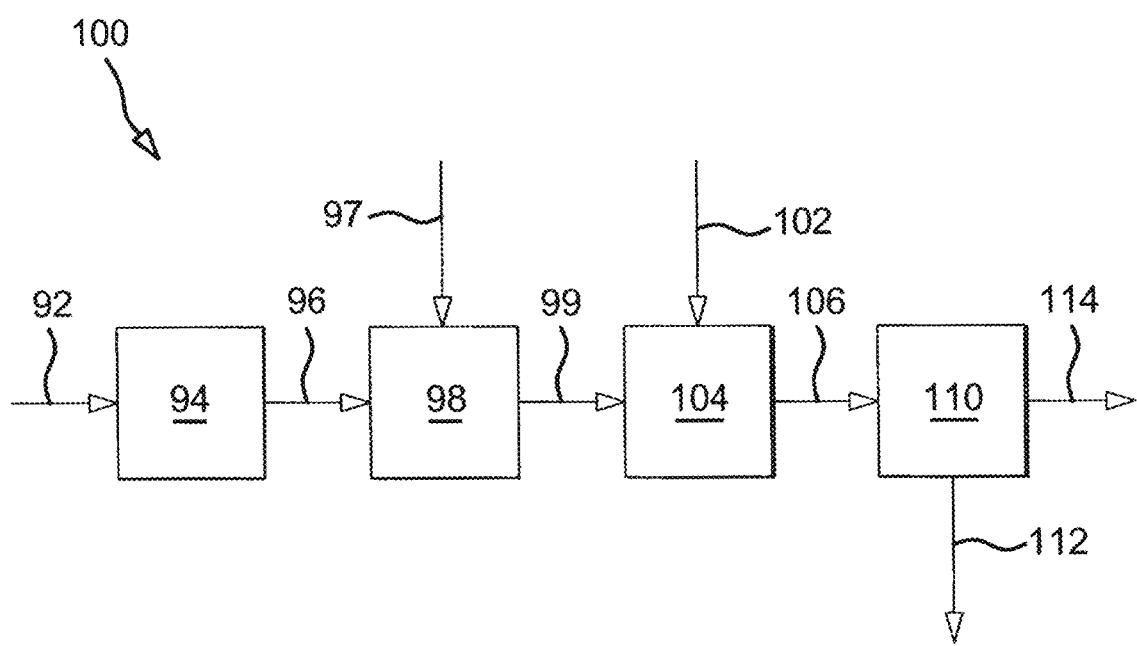

METHODS OF PREPARING OLIGOMERS OF AN OLEFIN

REFERENCE TO RELATED APPLICATIONS

This application is a national stage application under 35 USC 371 of International Application No. PCT/RU2014/000973, filed Dec. 23, 2014, the entire contents of which are incorporated herein by reference.

BACKGROUND OF THE INVENTION

Field of the Disclosed Subject Matter

The presently disclosed subject matter relates to methods of preparing oligomers of an olefin. For example, the presently disclosed subject matter provides methods of preparing 1-hexene from ethylene. The methods can include irradiation of an alkylaluminum compound and/or other components of a catalyst composition, and incorporation of a zinc compound into the catalyst composition.

Description of Related Art

Oligomerization of olefins can produce many valuable chemical products. For example, simple feedstock olefins can be oligomerized to provide useful higher olefins. Industrially important processes include the preparation of alpha olefins ($\alpha$ olefins) from ethylene, e.g., the preparation of 1-hexene via trimerization of ethylene.

A problem encountered in some oligomerizations of olefins can be incomplete selectivity for the desired oligomer. That is, in addition to the desired oligomer, side products and byproducts can be formed. The side products and byproducts can include other oligomers as well as polymers. As an example, in oligomerization of ethylene to 1-hexene, other isomers of hexene (trans-2-hexene, cis-2-hexene, trans-3-hexene, and cis-3-hexene, which can together be referred to as "internal olefins") can be formed, as well as higher oligomers of ethylene (e.g., octene, decene, and dodecene) and polyethylene.

Internal olefins can be undesirable impurities in an $\alpha$ olefin product. For example, the internal olefins 2-hexene and 3-hexene can be undesirable impurities in 1-hexene. Unlike 1-hexene, 2-hexene and 3-hexene do not copolymerize with ethylene under standard conditions for preparation of linear low-density polyethylene (LLDPE) and high-density polyethylene (HDPE). 2-Hexene and 3-hexene can also degrade the performance of catalysts used for polymerization. Therefore, it can be desirable to prepare 1-hexene with low levels of 2-hexene and 3-hexene.

Preparation of $\alpha$ olefins with low levels of internal olefins can be achieved by separation of the internal olefins. Such separation can be difficult, as internal olefins and their corresponding $\alpha$ olefins can often have similar chemical properties. For example, 1-hexene, trans-2-hexene, cis-2-hexene, trans-3-hexene, and cis-3-hexene have similar boiling points. Separation of hexene isomers by rectification (distillation) can consequently be inefficient and energy intensive. Separation of hexene isomers by rectification (distillation) can require a high number of theoretical plates, a high reflux ratio, and high-powered bottom exchangers (reboilers), all of which can increase the cost of purification. Super C6 (1-hexene superfractionation) columns are often used to separate 1-hexene from internal olefin isomers, and such columns are expensive.

To reduce the cost of separation of internal olefins from the corresponding $\alpha$ olefins, it can be desirable to develop selective processes that generate $\alpha$ olefins with only minimal amounts of the corresponding internal olefins. Various attempts have been made to develop olefin oligomerization processes that are highly selective for $\alpha$ olefins. For example, U.S. Pat. Nos. 8,252,955 and 8,252,956, the contents of which are hereby incorporated by reference in their entirety, describe catalysts and processes for selective preparation of 1-hexene via trimerization of ethylene, but the catalysts disclosed require expensive ligands and use of methylaluminoxane (MAO) and/or modified methylaluminoxane (MMAO). International (PCT) Patent Application Publication No. WO 99/19280, the contents of which are hereby incorporated by reference in their entirety, discloses trimerization of ethylene to 1-hexene with up to 99.6:0.4 selectivity for 1-hexene over internal olefin isomers with a catalyst that includes a chromium compound, an alkylaluminum compound, and a pyrrole ligand. U.S. Pat. No. 6,455,648, the contents of which are hereby incorporated by reference in their entirety, similarly discloses trimerization of ethylene to 1-hexene with up to 99.6:0.4 selectivity for 1-hexene over internal olefin isomers with a catalyst that includes a chromium compound, an alkylaluminum compound, and a pyrrole ligand. However, these catalyst compositions can have drawbacks. For example, existing catalysts that are selective for 1-hexene can also promote formation of undesirable polymer (polyethylene) side product. See, for example, Yang et al., Applied Catalysis A: General (2000) 193:29-38.

Incorporation of a zinc compound into a catalyst composition used in olefin oligomerization has been reported. For example, International (PCT) Patent Application Publication No. WO 2011/140629, the contents of which are hereby incorporated by reference in their entirety, describes trimerization of ethylene to 1-hexene with catalysts that include chromium, an alkylaluminum compound, and a zinc compound. However, the maximal selectivity for 1-hexene over internal isomers of hexene achievable with the disclosed catalysts is only about 96:4.

There remains a need for methods of preparing oligomers of an olefin with increased selectivity for a desired $\alpha$ olefin isomer over internal olefin isomers and other beneficial characteristics. It is therefore desirable to provide catalysts and processes that achieve improved selectivity, reduced side product and by-product formation, improved yields of the desired $\alpha$ olefin, improved economy, and improved efficiency.

SUMMARY OF THE INVENTION

The purpose and advantages of the disclosed subject matter will be set forth in and apparent from the description that follows, as well as will be learned by practice of the disclosed subject matter. Additional advantages of the disclosed subject matter will be realized and attained by the methods and techniques particularly pointed out in the written description and the claims hereof, as well as from the appended drawing.

To achieve these and other advantages and in accordance with the purpose of the disclosed subject matter, as embodied and broadly described, the disclosed subject matter provides methods of preparing oligomers of an olefin, including methods of preparing 1-hexene from ethylene.

In accordance with the disclosed subject matter, methods of preparing oligomers of an olefin are provided. An exemplary method can include providing an alkylaluminum compound and irradiating the alkylaluminum compound with microwave radiation to provide an irradiated alkylaluminum compound. The method can further include mixing the irradiated alkylaluminum compound with a chromium compound, a pyrrole compound, and a zinc compound to provide a catalyst composition. The method can further include contacting an olefin with the catalyst composition to form oligomers of the olefin.

For example, and as embodied herein, mixing of the irradiated alkylaluminum compound with the chromium compound can occur within 10 minutes of irradiation. Furthermore, mixing of the irradiated alkylaluminum compound with the chromium compound can occur within 3 minutes of irradiation.

A further exemplary method of preparing oligomers of an olefin can include providing a mixture of an alkylaluminum compound and a zinc compound and irradiating the mixture with microwave radiation to provide an irradiated mixture. The method can further include mixing the irradiated mixture with a chromium compound and a pyrrole compound to provide a catalyst composition and contacting an olefin with the catalyst composition to form oligomers of the olefin.

For example, and as embodied herein, mixing of the irradiated mixture with the chromium compound can occur within 10 minutes of irradiation. Furthermore, mixing of the irradiated mixture with the chromium compound can occur within 3 minutes of irradiation.

In some embodiments, the alkylaluminum compound can include at least one alkylaluminum compound selected from the group consisting of triethylaluminum and diethylaluminum chloride. The zinc compound can include a dialkylzinc compound. The dialkylzinc compound can include diethylzinc.

For example, and as embodied herein, the microwave radiation can include a frequency in a range from about 0.2 GHz to about 20 GHz. The microwave radiation can include a frequency of about 2.45 GHz. Furthermore, the olefin can include ethylene. In some embodiments, the oligomers of the olefin can include 1-hexene. The oligomers of the olefin can further include other isomers of hexene, and the ratio of 1-hexene to other isomers of hexene can be at least 99.7:0.3. Additionally, methods of preparing oligomers of an olefin can include contacting the olefin and the composition with hydrogen.

In accordance with the disclosed subject matter, methods of preparing 1-hexene from ethylene are provided. An exemplary method can include contacting ethylene with a catalyst to provide 1-hexene and other isomers of hexene. The ratio of 1-hexene to other isomers of hexene can be at least 99.7:0.3.

It is to be understood that both the foregoing general description and the following detailed description are exemplary and are intended to provide further explanation of the disclosed subject matter claimed.

The accompanying drawing, which is incorporated in and constitutes part of this specification, is included to illustrate and provide a further understanding of the disclosed subject matter. Together with the description, the drawing serves to explain the principles of the disclosed subject matter.

BRIEF DESCRIPTION OF THE DRAWINGS

The FIGURE is a schematic representation illustrating an exemplary system that can be used in conjunction with the methods of the disclosed subject matter.

While the disclosed subject matter is described below in detail with reference to the FIGURE, it is done so in connection with the illustrative embodiments and not by way of limitation.

DETAILED DESCRIPTION OF THE INVENTION

The methods presented herein can be used for various oligomerization processes, including, but not limited to, olefin oligomerizations, e.g., trimerization or tetramerization of ethylene. The methods can be used on relatively small scale, e.g., laboratory scale or bench scale, and can be used on relatively large scale, e.g., industrial scale. Oligomerization can occur in a homogeneous or colloidal solution. Oligomerization can occur in various reactors known in the art, as described in more detail below. Oligomerization can occur in more than one reactor operated in series or parallel. For purpose of illustration only and not limitation, and as embodied herein, the methods presented can be used in the context of trimerization of ethylene to 1-hexene.

As used herein, the term "alkyl" refers to saturated aliphatic groups. Alkyl groups can be straight chain (e.g., ethyl, n-propyl, n-butyl) or branched chain (e.g., i-propyl, s-butyl). The term "alkyl" also encompasses cycloalkyl groups, i.e., saturated aliphatic carbon-based cyclic groups. Cycloalkyl groups can include one ring or more than one ring. By way of non-limiting example, cycloalkyl groups can include cyclopropyl, cyclobutyl, cyclopentyl, cyclohexyl, cycloheptyl, and cyclooctyl.

As used herein, the terms "alkane" and "alkanes" refer to saturated aliphatic compounds. Alkyl compounds can be straight chain (e.g., ethane, propane, n-butane, n-hexane, n-octane, n-decane, n-undecane) or branched chain (e.g., i-butane, 3-methylnonane). Straight chain alkanes are also known as linear alkanes or n-alkanes and are acyclic alkanes without side chains. Branched chain alkanes, also known simply as "branched alkanes," are acyclic, non-linear alkanes with one or more side chains.

As used herein, the terms "alkane" and "alkanes" also encompass cycloalkane compounds, i.e., saturated aliphatic carbon-based cyclic compounds. Cycloalkanes can include one ring or more than one ring. By way of non-limiting example, cycloalkanes can include cyclopropane, cyclobutane, cyclopentane, cyclohexane, cycloheptane, cyclooctane, cyclononane, and cyclodecane. Cycloalkanes can be substituted. Exemplary substituted cycloalkanes include methylcyclopentane and methylcyclohexane.

As used herein, the term "halogen" refers to the Group 17 elements, i.e., fluorine, chlorine, bromine, iodine, and astatine.

As used herein, the terms "group" and "moiety" refer to parts of a larger composition, compound, molecule, or structure.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In accordance with the disclosed subject matter, methods of preparing oligomers of an olefin can generally include providing an alkylaluminum compound and irradiating the alkylaluminum compound with microwave radiation to provide an irradiated alkylaluminum compound. The method can further include mixing the irradiated alkylaluminum compound with a chromium compound, a pyrrole compound, and a zinc compound to provide a catalyst composition. The method can further include contacting an olefin with the catalyst composition to form oligomers of the olefin. In these methods, the alkylaluminum compound can be irradiated prior to mixing with the zinc compound and other components of the catalyst composition.

In accordance with the disclosed subject matter, methods of preparing oligomers of an olefin can generally include providing a mixture of an alkylaluminum compound and a zinc compound and irradiating the mixture with microwave radiation to provide an irradiated mixture. The method can further include mixing the irradiated mixture with a chromium compound and a pyrrole compound to provide a catalyst composition and contacting an olefin with the catalyst composition to form oligomers of the olefin. In these methods, the alkylaluminum compound can be mixed with the zinc compound prior to irradiation, and the resulting mixture can be irradiated before mixing with other components of the catalyst composition.

Reference will now be made in detail to the various exemplary embodiments of the disclosed subject matter, exemplary embodiments of which are illustrated in the accompanying drawing. The methods and corresponding techniques of the disclosed subject matter will be described in conjunction with the detailed description.

The accompanying FIGURE serves to further illustrate various embodiments and to explain various principles and advantages all in accordance with the disclosed subject matter. For purpose of explanation and illustration, and not limitation, exemplary embodiments of the methods of preparing oligomers of an olefin in accordance with the disclosed subject matter are shown in conjunction with the FIGURE. While the presently disclosed subject matter is described with respect to the system of the FIGURE and the Examples presented below, one skilled in the art will recognize that the disclosed subject matter is not limited to the illustrative embodiments, and that the methods and techniques described herein can be used to prepare oligomers of an olefin in any suitable reaction or system.

In accordance with the disclosed subject matter, with reference to the FIGURE, the presently disclosed methods can be performed in conjunction with an exemplary system 100. The system 100 can include a microwave 94 in which materials can be irradiated. The microwave 94 can be coupled to one or more feed lines 92. While one feed line 92 is shown in the FIGURE, it should be understood that multiple feed lines can be coupled to the microwave 94. The feed line(s) 92 can feed various components to the microwave 94. In some embodiments, the components fed to the microwave 94 can include an alkylaluminum compound and a solvent.

In some embodiments, the components fed to the microwave 94 can further include a zinc compound. An irradiated composition stream 96 containing an irradiated composition can be removed from the microwave 94. The irradiated composition stream 96 can include an irradiated alkylaluminum compound. The irradiated composition stream 96 can further include an irradiated zinc compound. That is, the irradiated composition stream 96 can include an irradiated mixture that includes both an irradiated alkylaluminum compound and an irradiated zinc compound.

In other embodiments, the components fed to the microwave 94 can include an alkylaluminum compound but no zinc compound. As shown in the FIGURE, the system 100 can optionally include a catalyst mixing unit 98, and the irradiated composition stream 96 can be coupled to the catalyst mixing unit 98. The catalyst mixing unit 98 can be further coupled to one or more feed lines 97. The feed line(s) 97 can feed a zinc compound, a transition metal source (e.g., a chromium compound), a halogenic compound, and/or a pyrrole compound to the catalyst mixing unit 98. When a catalyst mixing unit 98 is present in the system 100, the catalyst mixing unit can mix an irradiated alkylaluminum compound derived from the irradiated composition stream 96 with other catalyst components to provide a catalyst composition. The catalyst composition which can be removed from the catalyst mixing unit 98 through a catalyst stream 99. When the system 100 includes a catalyst mixing unit 98, the alkylaluminum compound can be irradiated individually, prior to mixing with other catalyst components.

The system 100 can also include a reactor 104 in which an olefin oligomerization reaction can be conducted. The reactor 104 can be coupled to one or more feed lines 102. The reactor 104 can be further coupled directly to the irradiated composition stream 96. Alternatively, when a catalyst mixing unit 98 is present, the reactor 104 can be coupled to the catalyst stream 99, as shown in the FIGURE. While one feed line 102 is shown in the FIGURE, it should be understood that multiple feed lines can be coupled to the reactor 104. The feed line(s) 102 can feed various components to the reactor 104. In some embodiments, the components fed to the reactor 104 can include an organometallic catalyst, a transition metal source, a zinc compound, a pyrrole compound, an olefin, hydrogen, and/or one or more solvents. By way of non-limiting example, in some embodiments there can be one or more feed lines feeding an organometallic catalyst solution, one or more feed lines feeding solvent(s), one or more feed lines feeding an olefin (e.g., ethylene), and/or one or more feed lines feeding hydrogen. The irradiated composition stream 96, the catalyst stream 99, and/or various components fed through feed line(s) 102 can be mixed within the reactor 104 to provide a combined catalyst composition and reaction mixture. When the irradiated composition stream 96 is coupled to the reactor 104 and no catalyst mixing unit 98 is present, the irradiated composition stream 96 can be pre-mixed with one or more components fed through feed line(s) 102 (e.g., a chromium compound) before being fed to the reactor 104. Alternatively, when a catalyst mixing unit 98 is present, the catalyst stream 99 can be pre-mixed with one or more components fed through feed line(s) 102 (e.g., a solvent) before being fed to the reactor 104.

An olefin oligomerization reaction can occur in the reactor 104, to provide oligomerization products as well as side products and by-products (e.g., polymer). An effluent stream 106 containing oligomerization products (oligomers of the olefin) as well as side product polymer and organometallic catalyst can be removed from the reactor 104. In some embodiments, the effluent stream 106 can be cooled. In some embodiments, a deactivating agent (e.g., water) and/or a sorbent can be added to the effluent stream 106. Further description of sorbents that can be used in accordance with the disclosed subject matter is provided in International (PCT) Application No. PCT/RU2014/000972, filed Dec. 23, 2014, which is hereby incorporated by reference in its entirety. A deactivating agent can deactivate the organometallic catalyst to provide a deactivated catalyst. Cooling the effluent stream 106, adding a deactivating agent, and/or adding a sorbent can precipitate polymer as well as deactivated catalyst. Precipitate containing sorbent, polymer, and/or deactivated catalyst can optionally be separated in a separation unit 110, to provide precipitate 112 and a purified product stream 114.

Microwave irradiation of alkylaluminum compounds and other materials is generally described in United States Patent Application Publication No. US 2012/0302715, the contents of which are hereby incorporated by reference in their entirety. By way of non-limiting example, the microwave 94 can be a microwave flow irradiator. For example, and as embodied in the Examples below, the microwave flow irradiator can be a tubular displacement reactor (e.g., a perfluoroalkoxy alkanes (PFA) tubular displacement reactor) positioned with a microwave resonance chamber. The microwave 94 can include a non-irradiation zone as well as an irradiation zone. In some embodiments, the microwave 94 can have a rated power of about 800 W. In some embodiments, the power can be between about 800 W to about 1500 W per mole of elemental aluminum.

By way of non-limiting example, materials fed into the microwave 94 (e.g., an alkylaluminum compound or a mixture of an alkylaluminum compound and a zinc compound) can be irradiated with microwave radiation of a frequency between about 0.2 GHz and 20 GHz. In some embodiments, the microwave radiation can include or have a frequency of about 2.45 GHz. The duration of irradiation can be between about 0.5 minutes (30 seconds) and about 20 minutes. In some embodiments, the duration of irradiation can be about 0.5 minutes, about 1 minute, about 2 minutes, about 3 minutes, about 4 minutes, about 5 minutes, about 6 minutes, about 8 minutes, about 10 minutes, about 12 minutes, about 15 minutes, or about 20 minutes. In some embodiments, the duration of irradiation can be about 4 minutes.

The irradiated composition stream 96 (which can include an irradiated alkylaluminum compound or an irradiated mixture that contains an alkylaluminum compound and an irradiated zinc compound) can be removed from the microwave 94. It can be advantageous to limit the time that elapses between irradiation and feeding the irradiated composition, or a mixture including the irradiated composition, to the reactor 104. For example, in some embodiments the time between irradiation and feeding the irradiated composition to the reactor 104 can be less than 10 minutes, less than 5, or less than 3 minutes. Upon feeding the irradiation composition to the reactor 104, a catalyst composition can be formed within the reactor 104. Alkylaluminum compounds can be irradiated to increase their activity and to increase the overall activity of an organometallic catalyst in the reactor 104.

One or more alkylaluminum compounds can be irradiated in the microwave 94. In some embodiments, the alkylaluminum compound can be an activator of a transition metal-based catalyst center (e.g., a chromium center). Alkylaluminum compounds can include halogenated alkylaluminum compounds, alkoxyalkylaluminum compounds, and mixtures thereof. Alkylaluminum compounds are compounds that include at least one aluminum-alkyl bond and, in some nonlimiting embodiments, can be represented by the general formulas $AlR_3$, $AlR_2X$, $AlRX_2$, $AlR_2OR$, $AlRXOR$, or $Al_2R_3X_3$, where R is an alkyl group and X is a halogen atom (e.g., Cl or Br). Nonlimiting examples of alkylaluminum compounds include trimethylaluminum, triethylaluminum, tripropylaluminum, tributylaluminum, diethylaluminum chloride, ethylaluminum dichloride, ethylaluminum sesquichloride, and methylaluminoxane (MAO). Alkylaluminum compounds can be used as mixtures of multiple alkylaluminum compounds. In some embodiments, the alkylaluminum compound can be triethylaluminum or a mixture of triethylaluminum and diethylaluminum chloride. The alkylaluminum compound can be used as a solution in a solvent, e.g., in a hydrocarbon solvent.

In accordance with the disclosed subject matter, an alkylaluminum compound can be heated (e.g., to about 80° C.) prior to irradiation. In some embodiments, an irradiated alkylaluminum compound (e.g., an irradiated composition that includes an irradiated alkylaluminum compound) can be heated (e.g., to about 80° C.) prior to being fed into the reactor 104. Without being bound to any particular theory, it can be that pre-heating of the irradiated alkylaluminum compound can shift the equilibrium between alkylaluminum oligomers (e.g., dimers) and monomers in favor of alkylaluminum monomers. In some embodiments, alkylaluminum monomers can better coordinate to transition metal (e.g., chromium) centers and can increase catalytic activity.

One or more zinc compounds can be irradiated in the microwave 94. One or more zinc compounds can also be added directly to the catalyst mixing unit 98 and/or the reactor 104 without irradiation, e.g., through a feed line 102. In some embodiments, the zinc compound can be an activator of a transition metal-based catalyst center (e.g., a chromium center). In some embodiments, the zinc compound can include metallic zinc (Zn(0)), zinc-copper couples, alkylzinc compounds (including dialkylzinc compounds), arylzinc compounds (including diarylzinc compounds), zinc amides (e.g., zinc pyrrolides or zinc porphyrin complexes), zinc oxygenates (e.g., zinc formates, zinc acetates, zinc 2-ethylhexanoates, and other zinc carboxylates), zinc halides (e.g., anhydrous zinc chloride), and combinations thereof. In some embodiments, the zinc compound can include a dialkylzinc compound. In some embodiments, the dialkylzinc compound can include dimethylzinc, diethylzinc, dibutylzinc, and mixtures thereof. In some embodiments, the zinc compound can include a diarylzinc compound. In some embodiments, the diarylzinc compound can include diphenylzinc, ditolylzinc, and mixtures thereof. It can be advantageous to use a zinc compound that is soluble in the solvents used in the methods of the presently disclosed subject matter, e.g., in hydrocarbon solvents. The zinc compound can be used as a solution in a solvent, e.g., in a hydrocarbon solvent.

The olefin oligomerization reactions of the presently disclosed subject matter can be performed in various reactors known in the art. By way of non-limiting example, suitable reactors 104 can include continuous stirred-tank reactors, batch reactors, plug flow reactors, and pipe or tubular reactors (laminar flow reactors). The reactor 104 can be a reactor suitable for gas/liquid reactions, e.g., an autoclave reactor with an agitator, a bubble column reactor (bubbling reactor) with straight-flow or counter-flow gas and liquid supply, or a bubbling gas lift reactor. The reactor can include components and accessories not depicted in the FIGURE, such as, for example, one or more additional feed lines, one or more gas inlet lines, one or more gas outlet lines, one or more flue gas exhaust lines, one or more agitators, a reaction zone, one or more heating elements, and/or one or more viscometers. The components and accessories can be placed at various locations on the reactor, as known in the art.

In some embodiments, the organometallic catalyst in the reactor 104 can include one or more transition metal sources. By way of non-limiting example, the transition metal(s) can include Ti, Zr, Hf, Ni, Cr, Fe, Co, Pd, Pt, and combinations thereof. In accordance with the disclosed subject matter, the organometallic catalyst can include chromium (Cr). The organometallic catalyst can be a homogenous catalyst or a heterogeneous catalyst.

When the organometallic catalyst includes chromium, the source of chromium can be organic chromium compounds and/or inorganic chromium compounds. The oxidation state of the chromium source can vary. For example, chromium sources can include compounds in which chromium is in the oxidation states 0, +1, +2, +3, +4, +5, and +6. Generally, the chromium source can be a chromium compound of the formula $CrX_n$, where the X substituents are the same or different and where n is a number from 1 to 6. The X substituents can be organic or inorganic radicals. By way of non-limiting example, suitable organic radicals X can include from 1 to 20 carbon atoms and can include alkyl groups, alkoxy groups, carboxy groups, acetylacetonate groups, amino groups, and amido groups. By way of non-limiting example, suitable inorganic radicals X can include halogens (to form a chromium halide), sulfate (to form a chromium sulfate), and oxygen (to form a chromium oxide). Examples of chromium sources can include chromium(III) chloride, chromium(III) acetate, chromium(III) tris-ethylhexanoate, chromium(III) acetylacetonate, chromium(III) pyrrolide, chromium(II) acetate, and chromyl chloride ($CrO_2Cl_2$).

The organometallic catalyst in the reactor 104 can further include one or more halogenic compounds. The halogenic compound can be described as a halide source. The halogenic compounds can be compounds of formula $R_mX_n$, wherein R is an organic, organometallic, or inorganic radical, X is a halogen (e.g., F, Cl, Br, or I), and the sum (m+n) is greater than 0. Exemplary halogenic compounds can include $AlEt_2Cl$, $AlEtCl_2$, $AlCl_3$, dibutylaluminum chloride, diethylaluminum bromide, diethylaluminum iodide, butyl bromide, dichloromethane, carbon tetrachloride, $CHCl_3$ (chloroform), hexachloroethane, boron trichloride, and germanium tetrachloride. Addition of one or more halogenic compounds can improve the selectivity, activity, and/or productivity of the organometallic catalyst.

The organometallic catalyst in the reactor 104 can further include a pyrrole compound. In some embodiments, the pyrrole compound can coordinate to a transition metal and serve as a ligand. The pyrrole compound can be a compound that includes a pyrrole moiety, i.e., a five-membered aromatic heterocycle that contains a single nitrogen atom. By way of non-limiting example, pyrrole compounds include pyrrole, 2,5-dimethylpyrrole, lithium pyrrolide ($C_4H_4NLi$), 2-ethylpyrrole, indole, 2-methylindole, and 4,5,6,7-tetrahydroindole. In some embodiments, the pyrrole compound can be pyrrole or 2,5-dimethylpyrrole.

The organometallic catalyst in the reactor 104 can be varied, as is understood in the art. For example, when an alkylaluminum compound, a chromium compound, and a pyrrole compound are used, the molar ratios of aluminum to chromium and pyrrole compound to chromium can be varied. example, and as embodied herein, the aluminum to chromium ratio can vary from about 10:1 to about 2000:1, e.g., from about 20:1 to about 300:1. For example, and as embodied herein, the pyrrole compound to chromium ratio can vary from about 2:1 to about 100:1, e.g., from about 3:1 to about 7:1. For example, and as embodied herein, the ratio of any additional halogenic compound to chromium can vary from about 1:1 to about 150:1, e.g., from about 8:1 to about 16:1, as calculated on the basis of elemental halogen. When a zinc compound is used in conjunction with an alkylaluminum compound and chromium compound, the ratio of zinc compound to chromium compound can be varied. For example, and as embodied herein, the zinc to chromium ratio can vary from about 2:1 to about 1000:1, e.g., from about 5:1 to about 200:1. In some embodiments, the zinc to chromium ratio can be about 12:1, about 25:1, or about 50:1. In some embodiments, a smaller molar quantity of alkylaluminum compound can be used when a zinc compound is included in the organometallic catalyst within the reactor 104.

Olefins useful for olefin oligomerization can include simple feedstock olefins, e.g., ethylene (ethene), propylene (propene), and butylene (butene). In some embodiments, the olefin can be ethylene. Olefins can be oligomerized to provide useful higher olefins. Industrially important processes include preparation of alpha olefins (α olefins) from ethylene. Alpha olefins are olefin compounds with a carbon-carbon double bond (C=C) at the primary or alpha position. Alpha olefins prepared from oligomerization can include various $C_5$-$C_{40}$ olefins and mixtures thereof. For example, alpha olefins prepared from oligomerization can include 1-pentene, 1-hexene, 1-heptene, 1-octene, 1-nonene, 1-decene, 1-undecene, 1-dodecene, 1-tridecene, 1-tetradecene, higher alpha olefins, and mixtures thereof. In accordance with the disclosed subject matter, the olefin oligomerization reaction can include a trimerization of ethylene to 1-hexene.

When the olefin oligomerization in the reactor 104 is a trimerization of ethylene to 1-hexene, the pressure of ethylene used is variable, as is understood in the art. For example, and as embodied herein, the ethylene pressure can be varied between about 1 to about 200 bar. In some embodiments, the ethylene pressure can be greater than 4 bar. In some embodiments, in can be advantageous to increase the ethylene pressure to increase the rate of oligomerization.

In some embodiments of the presently disclosed subject matter, the temperature with the reactor 104 can be between about 0° C. and about 160° C. In some embodiments, the temperature within the reactor 104 can be between about 40° C. and about 120° C. For example, when the olefin oligomerization in the reactor 104 is a trimerization of ethylene to 1-hexene, the temperature of the reactor can be between about 40° C. and about 120° C., e.g., at about 100° C. In some embodiments, and as described herein, it can be advantageous to maintain a reaction temperature above about 80° C., e.g., above about 95° C. At such temperatures, polymer side products (e.g., polyethylene) can remain fully dissolved in the solvent and the organometallic catalyst can remain active and selective. By way of non-limiting example, in some trimerization reactions of ethylene to 1-hexene, lower temperatures (e.g., temperatures below about 80° C.) can cause polyethylene to precipitate from solution.

In accordance with the disclosed subject matter, reaction time can be varied as understood in the art. The reaction time can be defined as the residence time of the feedstock and solvent in the oligomerization reaction zone. In the case of continuous flow reactors, the reaction time can be the mean residence time, as understood in the art. The reaction time can vary depending on olefin used, reaction temperature, reaction pressure, and other parameters of the reaction. In some embodiments, the reaction can be terminated in less than a day. In some embodiments, reaction time can be shorter, e.g., less than 12 hours, less than 6 hours, less than 3 hours, less than 2 hours, less than 1 hour, less than 30 minutes, less than 15 minutes, less than 10 minutes, less than 5 minutes, less than 3 minutes, less than 2 minutes, less than 1 minute, less than 30 seconds, less than 15 seconds, less than 10 seconds, less than 5 seconds, less than 3 seconds, or about 1 second. In some embodiments, when the olefin is ethylene and the oligomerization is a trimerization of ethylene to form 1-hexene, the reaction time can be about 30 minutes or about 60 minutes.

In accordance with the disclosed subject matter, an olefin and a catalyst composition (e.g., a composition that includes an alkylaluminum compound, a chromium compound, and a hydrocarbon solvent) can be contacted with hydrogen. Hydrogen can be fed into the reactor 104. In some embodiments, hydrogen can serve as a diluent. Hydrogen can accelerate the oligomerization reaction and/or increase activity of the organometallic catalyst. In some embodiments, hydrogen can reduce the amount of side product polymer formed and limit deposition (precipitation) of polymer within the reactor 104 and in downstream equipment. For example, in the oligomerization of ethylene to 1-hexene, hydrogen can reduce formation of polyethylene and discourage deposition of polyethylene.

One or more solvents can be used in oligomerization of olefins in the reactor 104. The solvent can include one or more hydrocarbon compounds. The hydrocarbon compounds can include alkane compounds, including straight chain alkanes, branched alkanes, and cycloalkanes. The hydrocarbon compounds can also include alkene compounds (e.g., 1-hexene) and/or arene (aromatic) compounds (e.g., benzene and toluene). The hydrocarbon compounds can be a mixture of hydrocarbons, e.g., kerosene. The hydrocarbon compounds can be C4-C12 hydrocarbons. By way of non-limiting example, the solvent can include cyclohexane, methylcyclohexane, heptane (and isomers thereof), cycloheptane, octane (and isomers thereof), cyclooctane, nonane (and isomers thereof), cyclononane, decane (and isomers thereof), cyclodecane, undecane (and isomers thereof), cycloundecane, dodecane (and isomers thereof), cyclododecane, and combinations thereof. Further description of solvents that can be used in accordance with the disclosed subject matter is provided in International (PCT) Application No. PCT/RU2014/000974, filed Dec. 23, 2014, which is hereby incorporated by reference in its entirety. In some embodiments, solvents can be preheated prior to use. For example, solvents can be preheated to a temperature approximately equal to the reaction temperature, e.g., about 100° C.

In some embodiments, more than one hydrocarbon compound can be used as solvent, and different mixtures of solvent can be used to prepare various solutions. For example, in some embodiments, a first solvent (e.g., n-octane) can be used to dissolve a zinc compound, a second solvent can be used to dissolve an alkylaluminum compound, and a third solvent can be used to dissolve other components of a catalyst composition. All solvents can be combined and/or optionally mixed with a fourth solvent in the reactor 104 to provide a combined reaction solvent.

In some embodiments, the reaction solvent in the reactor 104 can include one or more of heptane, cyclohexane, n-decane, n-undecane, and 1-hexene. In some embodiments, it can be desirable to use a reaction solvent that includes about 2% or less aromatic components. Without being bound to any particular theory, it can be that a reaction solvent that includes about 2% or less aromatic components can provide higher catalytic activity than a reaction solvent with a larger quantity of aromatic components.

In accordance with the disclosed subject matter, in some embodiments, components of the solvent(s) used can be selected on the basis of their boiling points. For example, alkane compounds having similar boiling points, which can boil within a relatively narrow temperature range (e.g., within about 10° C., about 20° C., about 30° C., or about 40° C.) can be used. Selection of alkane compounds having similar boiling points can facilitate separation; such compounds can be conveniently distilled away from desired olefin oligomerization products (e.g., 1-hexene). In methods of preparing 1-hexene from ethylene, it can be advantageous to avoid use of hexane as a solvent, as separation of hexane from 1-hexene by distillation can be difficult. Various mixtures of alkane compounds with similar boiling points can be commercially available, e.g., EXXSOL™ (EXXONMOBIL™) and ISOPAR™ (EXXONMOBIL™).

In accordance with the disclosed subject matter, various components present in the reactor 104 can be mixed in any order. By way of non-limiting example, an irradiated alkylaluminum compound can be mixed with a halogenic compound in a first hydrocarbon solvent to provide a first composition. The first composition can be mixed with a transition metal source (e.g., a chromium source) and a pyrrole compound in a second hydrocarbon solvent to provide a second composition, which can serve as an organometallic catalyst. A zinc compound can be added at any point, e.g., to the first composition or the second composition. A zinc compound can also be irradiated with an alkylaluminum compound to provide an irradiated mixture that includes both an irradiated zinc compound and an irradiated alkylaluminum compound, and the irradiated mixture can be combined with other catalyst components to provide an organometallic catalyst composition. The first hydrocarbon solvent and the second hydrocarbon solvent can be the same or different, and additional hydrocarbon solvents can be added. An olefin can then be contacted with the catalyst composition to form oligomers of the olefin.

In accordance with the disclosed subject matter, olefin oligomerization reactions can be conducted in the absence of water and oxygen. For example, water and oxygen can be excluded from the reactor 104.

In accordance with the disclosed subject matter, the effluent stream 106 from the olefin oligomerization reaction can include an organometallic catalyst, various products, byproducts, and side products from the olefin oligomerization reaction, and one or more solvents. The effluent stream can include polymers.

In some embodiments of the presently disclosed subject matter, polymers formed during olefin oligomerization can include polymers of the olefin being oligomerized. For example, polyethylene can form during oligomerization of ethylene.

One or more deactivating agents can be added to the effluent stream 106. Suitable deactivating agents known to one of skill in the art can be used, including water, alcohols, amines, amino alcohols, and combinations thereof. Exemplary alcohols can include methanol, ethanol, n-propanol, i-propanol, n-butanol, i-butanol, t-butanol, 2-butanol, 2-ethylhexanol, and combinations thereof. Exemplary amines can include ammonia, methylamine, dimethylamine, trimethylamine, ethylamine, diethylamine, triethylamine, tri-n-propylamine, diisopropylethylamine, tri-n-butylamine, piperazine, pyridine, ethylenediamine, diethylenetriamine, and combinations thereof. Exemplary amino alcohols can include ethanolamine, diethanolamine, triethanolamine, methyldiethanolamine, dodecyldiethanolamine, 1-amino-2-propanol, and combinations thereof. In accordance with the disclosed subject matter, the deactivating agent can be water.

In some embodiments, the effluent stream 106 can be cooled. Cooling the effluent stream can include removing the effluent stream from a heat source, e.g., removing the effluent stream from a heated reactor. Cooling the effluent stream can also include passing the effluent stream through a cooling unit, e.g., a heat exchanger. Cooling the effluent stream can include mixing a hot effluent stream with a cooled effluent stream. Cooling the effluent stream can include cooling the effluent stream to a temperature in a range between 100° C. and 20° C., e.g., to less than about 95° C., about 90° C., about 85° C., about 80° C., about 75° C., about 70° C., about 65° C., about 60° C., about 55° C., about 50° C., about 45° C., about 40° C., about 35° C., about 30° C., or about 25° C. Cooling the effluent stream can include cooling the effluent stream to ambient temperature, e.g., to a temperature in a range from about 20° C. to about 25° C. Cooling the effluent stream can include exposing the effluent stream to air. In some embodiments, the effluent stream can be cooled to a temperature between about 70° C. and about 20° C. The temperature to which the effluent stream is cooled can be selected to induce precipitation of the polymer while also avoiding excessive energy consumption during the cooling process. By way of non-limiting example, the effluent stream can be cooled from about 110° C. to about 70° C. in a settler-cooler, via recycling in a loop cooling stream with a temperature of about 40° C. and a residence time in the settler-cooler of about 1 hour.

In accordance with the disclosed subject matter, the methods of precipitating polymer and deactivated organometallic catalyst in an olefin oligomerization reaction can further include separating the precipitate from the effluent stream 106 to provide a purified product 114. Separation can provide separated precipitate 112 as well as the purified product 114. Separation can be performed via a separation unit 110. In some embodiments, the effluent stream can be cooled in the separation unit 110. In some embodiments, the separation unit can be one or more settling tanks, centrifugal separators, or filters, or a combination thereof. For example, and as embodied herein, precipitate can be concentrated in one or more settling tanks and periodically unloaded. Centrifugal separators can also be used to separate precipitate, with or without earlier concentration. Filtration can also be used to separate precipitate, with or without earlier concentration.

By way of non-limiting example, the effluent stream 106 can be cooled and solids (e.g., polymer and sorbent) settled under pressure. The effluent stream can then be filtered and sent to a deethenizer column, which can remove ethylene and hydrogen and send them to a recycling compressor. The filtered and degassed effluent can then be sent to a product isolation column, where 1-hexene can be distilled and isolated as the top product. Heavier compounds, including solvent and higher olefins, can be removed from the bottom of the product isolation column.

In some embodiments of the disclosed subject matter, olefin oligomerization reactions can be conducted with an organometallic catalyst that includes both an irradiated alkylaluminum compound and a zinc compound. It has been found that such catalysts can have surprising and unexpected advantages as compared to other catalysts. As shown in the Examples provided below, such catalysts have improved properties, including both increased activity and increased α olefin selectivity, as compared to catalysts that do not include an irradiated alkylaluminum compound and compared to catalysts that do not include a zinc compound. Such results demonstrate unexpected and synergistic benefits of the combination of an irradiated alkylaluminum compound with a zinc compound in the preparation of an organometallic catalyst for olefin oligomerization.

The catalysts and methods of the disclosed subject matter enable preparation of 1-hexene with a selectivity for 1-hexene over internal isomers of 99.7:0.3 or greater. Increased selectivity for 1-hexene provides the product in higher purity and reduces energy consumption during separation of 1-hexene from internal isomers. The catalysts and methods of the disclosed subject matter can also be used to prepare other α olefins.

In accordance with the disclosed subject matter, and as embodied herein, it can be particularly advantageous to combine an irradiated alkylaluminum compound with a zinc compound prior to the start of the olefin oligomerization reaction. Pre-mixing of an irradiated alkylaluminum compound with a zinc compound can improve catalyst selectivity and activity.

The disclosed subject matter enables preparation of 1-hexene from ethylene with improved selectivity via the use of simple, cheap reagents. Chromium-based catalysts can be used in conjunction with inexpensive pyrrole ligands, inexpensive zinc compounds, and inexpensive alkylaluminum compounds. PNP pincer ligands are not required. Non-hydrolyzed alkylaluminum compounds can be used. The selectivity and activity of the catalysts and methods of the disclosed subject matter can be at least comparable to the use of more expensive catalysts and methods that require use of PNP pincer ligands and partially hydrolyzed alkylaluminum compounds (e.g., MAO). As illustrated in the Examples below, catalytic activity in the range of about 30 to about 60 kg of ethylene consumed per gram chromium (Cr) per hour can be achieved.

EXAMPLES

The presently disclosed subject matter will be better understood by reference to the following Examples, which are provided as exemplary and not by way of limitation.

In all of the following Examples, product mixtures were analyzed by gas chromatography (GC). Catalytic activity was calculated based on the quantity of ethylene consumer per gram of chromium (Cr) present in the solution per hour, as measured by mass flow meter. The purity of 1-hexene is reported as the ratio of 1-hexene to the combined sum of all internal isomers of hexene, including cis- and trans-2-hexene and cis- and trans-3-hexene.

Example 1

Trimerization of Ethylene with Catalysts Prepared with an Irradiated Alkylaluminum Catalyst Preparation A mixture of 100 g of a 25% solution of triethylaluminum in hexane, by weight, and 80 g of 15% solution of diethylaluminum chloride in hexane, by weight, was pumped through a microwave flow irradiator with a rated power of 800 W. The microwave flow irradiator consisted of a PFA tubular displacement reactor positioned in a microwave resonance chamber. The solution residence time in the irradiator was 4 minutes, followed by 20 seconds in a non-irradiated zone. The mixture was pumped at a constant speed for 5 minutes into a solution of 3.50 g of 2,5-dimethylpyrrole (DMP) and 3.50 g of chromium(III) ethylhexanoate in 200 ml of ethylbenzene. After 30 minutes, the resulting mixture was evaporated in vacuum with stirring to remove >90% of the ethylbenzene. The resulting residue was diluted with cyclohexane to a total volume of 750 ml and a concentration of 0.5 mg Cr/ml.

Examples with No Zinc Compound

Example 1.A.1

Example with 4 ml of Catalyst Solution and n-Undecane Solvent

A 1 l steel reactor equipped with a heating/cooling jacket, an agitator, and gas and liquid inputs was provided. The reactor was evacuated and hydrogen was then dosed into the reactor to reach a pressure of 0.1 barg. 400 g of n-undecane was then pumped into the reactor. An aliquot (4 ml) of the catalyst solution prepared as described above was fed into the reactor with a syringe under a counter-flow of hydrogen. The propeller stirrer was switched on at 800 rpm. Hydrogen was dosed to reach pressure of 0.1 barg, and then ethylene was dosed to reach a total pressure in the reactor of 12.1 barg. The temperature in the reactor during the reaction was maintained at 100° C. with a thermostat, and ethylene was dosed to maintain pressure of 12.1 barg. After 60 minutes, a sample was taken from the reactor and the ethylene supply was cut off. The reactor was depressurized and cooled down to 40° C., and the contents were discharged (to provide an effluent stream).

Example 1.A.2

Example with 2 ml of Catalyst Solution and n-Undecane Solvent

A 1 l steel reactor equipped with a heating/cooling jacket, an agitator, and gas and liquid inputs was provided. The reactor was evacuated and hydrogen was then dosed into the reactor to reach a pressure of 0.1 barg. 400 g of n-undecane was then pumped into the reactor. An aliquot (2 ml) of the catalyst solution prepared as described above was fed into the reactor with a syringe under a counter-flow of hydrogen. The propeller stirrer was switched on at 800 rpm. Hydrogen was dosed to reach pressure of 0.1 barg, and then ethylene was dosed to reach a total pressure in the reactor of 12.1 barg. The temperature in the reactor during the reaction was maintained at 100° C. with a thermostat, and ethylene was dosed to maintain pressure of 12.1 barg. After 60 minutes, a sample was taken from the reactor and the ethylene supply was cut off. The reactor was depressurized and cooled down to 40° C., and the contents were discharged (to provide an effluent stream).

Example 1.A.3

Example with 3 ml of Catalyst Solution and Cyclohexane Solvent

A 1 l steel reactor equipped with a heating/cooling jacket, an agitator, and gas and liquid inputs was provided. The reactor was evacuated and hydrogen was then dosed into the reactor to reach a pressure of 0.1 barg. 400 g of cyclohexane was then pumped into the reactor. An aliquot (3 ml) of the catalyst solution prepared as described above was fed into the reactor with a syringe under a counter-flow of hydrogen. The propeller stirrer was switched on at 800 rpm. Hydrogen was dosed to reach pressure of 0.1 barg, and then ethylene was dosed to reach a total pressure in the reactor of 14.1 barg. The temperature in the reactor during the reaction was maintained at 100° C. with a thermostat, and ethylene was dosed to maintain pressure of 14.1 barg. After 30 minutes, a sample was taken from the reactor and the ethylene supply was cut off. The reactor was depressurized and cooled down to 40° C., and the contents were discharged (to provide an effluent stream).

Examples with a Zinc Compound

Example 1.B.1

Example with 4 ml of Catalyst Solution, 1 mmol Zn, and n-Undecane Solvent

A 1 l steel reactor equipped with a heating/cooling jacket, an agitator, and gas and liquid inputs was provided. The reactor was evacuated and hydrogen was then dosed into the reactor to reach a pressure of 0.1 barg. 400 g of n-undecane was then pumped into the reactor. An aliquot (4 ml) of the catalyst solution prepared as described above was fed into the reactor with a syringe under a counter-flow of hydrogen. A solution of diethylzinc in cyclohexane (1.0 M, 1 ml) was also fed into the reactor with a syringe. The propeller stirrer was switched on at 800 rpm. Hydrogen was dosed to reach pressure of 0.1 barg, and then ethylene was dosed to reach a total pressure in the reactor of 12.1 barg. The temperature in the reactor during the reaction was maintained at 100° C. with a thermostat, and ethylene was dosed to maintain pressure of 12.1 barg. After 60 minutes, a sample was taken from the reactor and the ethylene supply was cut off. The reactor was depressurized and cooled down to 40° C., and the contents were discharged (to provide an effluent stream).

Example 1.B.2

Example with 3 ml of Catalyst Solution, 1.5 mmol Zn, and Cyclohexane Solvent A 1 l steel reactor equipped with a heating/cooling jacket, an agitator, and gas and liquid inputs was provided. The reactor was evacuated and hydrogen was then dosed into the reactor to reach a pressure of 0.1 barg. 400 g of cyclohexane was then pumped into the reactor. An aliquot (3 ml) of the catalyst solution prepared as described above was fed into the reactor with a syringe under a counter-flow of hydrogen. A solution of diethylzinc in cyclohexane (1.0 M, 1.5 ml) was also fed into the reactor with a syringe. The propeller stirrer was switched on at 800 rpm. Hydrogen was dosed to reach pressure of 0.1 barg, and then ethylene was dosed to reach a total pressure in the reactor of 14.1 barg. The temperature in the reactor during the reaction was maintained at 100° C. with a thermostat, and ethylene was dosed to maintain pressure of 14.1 barg. After 30 minutes, a sample was taken from the reactor and the ethylene supply was cut off. The reactor was depressurized and cooled down to 40° C., and the contents were discharged (to provide an effluent stream).

The product (effluent stream) of each example was then analyzed to determine catalyst activity and selectivity for 1-hexene. The results of analysis are presented in Table 1 (n-undecane solvent) and Table 2 (cyclohexane solvent).

TABLE 1

|  | Example 1.A.1. (no zinc compound, 4 ml catalyst solution) | Example 1.A.2. (no zinc compound, 2 ml catalyst solution) | Example 1.B.1. (zinc compound included, 4 ml catalyst solution) |
| --- | --- | --- | --- |
| Catalytic activity over 60 minutes ((kg of ethylene consumed) per ((g Cr) * (hour))) | 23.2 | 67.4 | 36.2 |

TABLE 1-continued

|  | Example 1.A.1. (no zinc compound, 4 ml catalyst solution) | Example 1.A.2. (no zinc compound, 2 ml catalyst solution) | Example 1.B.1. (zinc compound included, 4 ml catalyst solution) |
|---|---|---|---|
| Molar ratio of 1-hexene to internal isomers of hexene | 98.1:1.9 | 99.0:1.0 | 99.3:0.7 |

TABLE 2

|  | Example 1.A.3. (no zinc compound, 3 ml catalyst solution) | Example 1.B.2. (zinc compound included, 3 ml catalyst solution) |
|---|---|---|
| Catalytic activity over 60 minutes ((kg of ethylene consumed) per ((g Cr) * (hour))) | 32.7 | 42.1 |
| Molar ratio of 1-hexene to internal isomers of hexene | 99.0:1.0 | 99.7:0.3 |

The data of Tables 1 and 2 demonstrates that the combination of an irradiated alkylaluminum compound and a zinc compound can provide catalysts with improved activity and selectivity. Addition of a zinc compound to the catalyst composition provided increased catalytic activity and increased selectivity for 1-hexene, as can be seen by comparing, for example, Example 1.B.1. to Example 1.A.1 and Example 1.B.2. to Example 1.A.3.

Example 2

Trimerization of Ethylene with Catalysts Prepared Without Irradiation

Catalyst Preparation

A mixture of 100 g of a 25% solution of triethylaluminum in hexane and 80 g of 15% solution of diethylaluminum chloride in hexane was pumped into a solution of 3.50 g of 2,5-dimethylpyrrole (DMP) and 3.50 g of chromium(III) ethylhexanoate in 200 ml of ethylbenzene. After 30 minutes, the resulting mixture was evaporated in vacuum with stirring to remove >90% of the ethylbenzene. The resulting residue was diluted with cyclohexane to a total volume of 750 ml and a concentration of 0.5 mg Cr/ml.

Examples with Cyclohexane Solvent

Examples 2.A.-2.E

A 0.3 l steel reactor equipped with a heating/cooling jacket, an agitator, and gas and liquid inputs was provided. The reactor was evacuated, and 114 g of cyclohexane was then loaded into the reactor using a pressure differential. The propeller stirrer was switched on at 800 rpm. Hydrogen was then dosed into the reactor to reach pressure of 0.1 barg. The solvent was heated to 100° C., and ethylene was dosed into the reactor to reach pressure of 12.1 barg. An aliquot of catalyst solution (2 ml) was fed into the reactor with a syringe under hydrogen pressure. An aliquot of a 1.0M solution of diethylzinc in cyclohexane was also fed into the reactor with a syringe. The volume of diethylzinc solution added in each experiment 2.A, 2.B, 2.C, 2.D, and 2.E is provided in Table 3. Examples 2.B and 2.C are duplicate experiments; both included addition of 0.25 ml of diethylzinc solution. Hydrogen was dosed to reach a pressure of 0.1 barg, then ethylene was dosed to reach pressure in the reactor of 12.1 barg. The temperature in the reactor was maintained at 100° C. throughout the reaction with a thermostat, and ethylene was dosed to maintain pressure of 12.1 barg. After 60 minutes, a sample was taken from the reactor and the ethylene supply was cut off. The reactor was depressurized and cooled down to 40° C., and the contents were discharged (to provide an effluent stream).

The products (effluent streams) of each experiment were then analyzed to determine catalyst activity and selectivity for 1-hexene. The results of analysis are presented in Table 3.

TABLE 3

| Example # | 2.A | 2.B | 2.C | 2.D | 2.E |
|---|---|---|---|---|---|
| Zinc (ml of 1.0M diethylzinc solution added) | 0 | 0.25 | 0.25 | 0.5 | 1 |
| Catalytic activity over 60 minutes ((kg of ethylene consumed) per ((g Cr) * (hour))) | 17.9 | 6.0 | 5.0 | 5.6 | 7.8 |
| Molar ratio of 1-hexene to internal isomers of hexene | 99.1:0.9 | 98.5:1.5 | 98.7:1.3 | 99.0:1.0 | 99.1:0.9 |

Examples with n-Undecane Solvent

Examples 2.F. & 2.G

A 0.3 l steel reactor equipped with a heating/cooling jacket, an agitator, and gas and liquid inputs was provided. The reactor was evacuated, and 114 g of n-undecane was then loaded into the reactor using a pressure differential. The propeller stirrer was switched on at 800 rpm. Hydrogen was then dosed into the reactor to reach pressure of 0.1 barg. The solvent was heated to 100° C., and ethylene was dosed into the reactor to reach pressure of 12.1 barg. An aliquot of catalyst solution (2 ml) was fed into the reactor with a syringe under hydrogen pressure. An aliquot of a 1.0M solution of diethylzinc in cyclohexane was also fed into the reactor with a syringe. The amount of diethylzinc solution added in each experiment 2.F & 2.G is presented in Table 4. Hydrogen was dosed to reach a pressure of 0.1 barg, then ethylene was dosed to reach pressure in the reactor of 12.1 barg. The temperature in the reactor was maintained at 100° C. throughout the reaction with a thermostat, and ethylene was dosed to maintain pressure of 12.1 barg. After 60 minutes, a sample was taken from the reactor and the ethylene supply was cut off. The reactor was depressurized and cooled down to 40° C., and the contents were discharged (to provide an effluent stream).

The products (effluent streams) of each experiment were then analyzed to determine catalyst activity and selectivity for 1-hexene. The results of analysis are presented in Table 4.

TABLE 4

| Experiment # | 2.F | 2.G |
|---|---|---|
| Zinc (ml of 1.0M diethylzinc solution added) | 0 | 1 |
| Catalytic activity over 60 minutes ((kg of ethylene consumed) per ((g Cr) * (hour))) | 12.3 | 6.5 |
| Molar ratio of 1-hexene to internal isomers of hexene | 98.6:1.4 | 98.6:1.4 |

For the purpose of illustration, the data of Tables 1-4 demonstrate that addition of a zinc compound to a catalyst composition prepared with an irradiated alkylaluminum provided unexpected and improved properties as compared to catalyst compositions that lack a zinc compound and/or an irradiated alkylaluminum. For example, use of a catalyst composition that included both a zinc compound and an irradiated alkylaluminum compound in trimerization of ethylene provided selectivity for 1-hexene over other isomers of hexene of 99.3:0.7 (Example 1.B.1) and 99.7:0.3 (Example 1.B.2), whereas use of catalyst compositions that lacked a zinc compound (Examples 1.A.1-1.A.3) or an irradiated alkylaluminum compound (Examples 2.A-2.G) provided lower selectivity of 99.1:0.9 or less.

Use of a catalyst composition that included both a zinc compound and an irradiated alkylaluminum compound in trimerization of ethylene also provided improved activity. For example, Examples 1.A.1 and 1.B.1 indicate that addition of diethylzinc to an otherwise identical reaction mixture in n-undecane solvent that lacked a zinc compound provided increased catalytic activity. In Example 1.B.1, which included diethylzinc, the catalytic activity was 36.2 (kg of ethylene consumed) per ((g Cr)*(hour)), whereas in Example 1.A.1, which did not include a zinc compound, the catalytic activity was 23.2 (kg of ethylene consumed) per ((g Cr)*(hour)). Similarly, Examples 1.A.3 and Example 1.B.2 indicate that addition of diethylzinc to an otherwise identical reaction mixture in cyclohexane solvent that lacked a zinc compound provided increased catalytic activity. In Example 1.B.2, which included diethylzinc, the catalytic activity was 42.1 (kg of ethylene consumed) per ((g Cr)*(hour)), whereas in Example 1.A.3, which did not include a zinc compound, the catalytic activity was 32.7 (kg of ethylene consumed) per ((g Cr)*(hour)).

The data presented in Tables 3 and 4 demonstrates that addition of a zinc compound to catalyst compositions prepared without an irradiated alkylaluminum does not provide increased activity or increased selectivity for 1-hexene. For example, in Example 2.A, which did not include a zinc compound, the catalytic activity was higher than in Examples 2.B-2.E, which did include a zinc compound. Selectivity for 1-hexene was equal or lower in Examples 2.B-2.E as compared to Example 2.A. Similarly, in Example 2.F, which did not include a zinc compound, the catalytic activity was higher than in Example 2.G, which did include a zinc compound. Selectivity for 1-hexene was unchanged between Examples 2.F and 2.G. Thus the Examples demonstrate that there are unexpected and synergistic benefits that arise from use of both a zinc compound and an irradiated alkylaluminum compound in catalysts for olefin oligomerization.

Additional Embodiments

Additionally or alternatively, the disclosed subject matter can include one or more of the following embodiments:

Embodiment 1

A method of preparing oligomers of an olefin, including providing an alkylaluminum compound, irradiating the alkylaluminum compound with microwave radiation to provide an irradiated alkylaluminum compound, mixing the irradiated alkylaluminum compound with a chromium compound, a pyrrole compound, and a zinc compound to provide a catalyst composition, and contacting an olefin with the catalyst composition to form oligomers of the olefin.

Embodiment 2

The method of the foregoing Embodiment, wherein mixing of the irradiated alkylaluminum compound with the chromium compound occurs within 10 minutes of irradiation.

Embodiment 3

The method of any of the foregoing Embodiments, wherein mixing of the irradiated alkylaluminum compound with the chromium compound occurs within 3 minutes of irradiation.

Embodiment 4

A method of preparing oligomers of an olefin, including providing a mixture of alkylaluminum compound and a zinc compound, irradiating the mixture with microwave radiation to provide an irradiated mixture, mixing the irradiated mixture with a chromium compound and a pyrrole compound to provide a catalyst composition, and contacting an olefin with the catalyst composition to form oligomers of the olefin.

Embodiment 5

The method of any of the foregoing Embodiments, wherein mixing of the irradiated mixture with the chromium compound occurs within 10 minutes of irradiation.

Embodiment 6

The method of any of the foregoing Embodiments, wherein mixing of the irradiated mixture with the chromium compound occurs within 10 minutes of irradiation.

Embodiment 7

The method of any of the foregoing Embodiments, wherein the alkylaluminum compound includes at least one alkylaluminum compound selected from the group consisting of triethylaluminum and diethylaluminum chloride.

Embodiment 8

The method of any of the foregoing Embodiments, wherein the zinc compound includes a dialkylzinc compound.

Embodiment 9

The method of any of the foregoing Embodiments, wherein the dialkylzinc compound include diethylzinc.

Embodiment 10

The method of any of the foregoing Embodiments, wherein the microwave radiation includes a frequency in a range from about 0.2 GHz to about 20 GHz.

Embodiment 11

The method of any of the foregoing Embodiments, wherein the microwave radiation includes a frequency of about 2.45 GHz.

Embodiment 12

The method of any of the foregoing Embodiments, wherein the olefin includes ethylene.

Embodiment 13

The method of any of the foregoing Embodiments, wherein the oligomers of the olefin include 1-hexene.

Embodiment 14

The method of any of the foregoing Embodiments, wherein the oligomers of the olefin further comprise other isomers of hexene, and the ratio of 1-hexene to other isomers of hexene is at least 99.7:0.3.

Embodiment 15

The method of any of the foregoing Embodiments, further including contacting the olefin and the catalyst composition with hydrogen.

Embodiment 16

A method of preparing 1-hexene from ethylene, including contacting ethylene with a catalyst to provide 1-hexene and other isomers of hexene, wherein the ratio of 1-hexene to other isomers of hexene is at least 99.7:0.3.

Embodiment 17

The method of any of the foregoing Embodiments, combined with the method of any other Embodiment.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the methods and systems of the disclosed subject matter without departing from the spirit or scope of the disclosed subject matter. Thus, it is intended that the disclosed subject matter include modifications and variations that are within the scope of the appended claims and their equivalents.

While the disclosed subject matter is described herein in terms of preferred embodiments, those skilled in the art will recognize that various modifications and improvements can be made to the disclosed subject matter without departing from the scope thereof. Moreover, although individual features of some embodiments of the disclosed subject matter can be discussed herein or shown in the drawings of those embodiments and not in other embodiments, it should be apparent that individual features of some embodiments can be combined with one or more features of another embodiment or features from a plurality of embodiments.

What is claimed is:

1. A method of preparing trimers of ethylene, comprising:
   providing an alkylaluminum compound;
   irradiating the alkylaluminum compound with microwave radiation to provide an irradiated alkylaluminum compound;
   mixing the irradiated alkylaluminum compound with a chromium compound, a pyrrole compound, and a zinc compound to provide a catalyst composition, the catalyst composition comprises the following molar ratios of: Al:Cr in a range from 20:1 to 300:1, Zn:Cr in a range from 5:1 to 200:1, and pyrrole compound:Cr in a range from 3:1 to 7:1; and
   contacting ethylene with the catalyst composition to form trimers of ethylene, wherein the trimers of ethylene comprise 1-hexene and other isomers of hexene, and a molar ratio of 1-hexene to the other isomers of hexene is at least 99.7:0.3.

2. The method of claim 1, wherein the mixing of the irradiated alkylaluminum compound with the chromium compound occurs within 10 minutes of irradiation.

3. The method of claim 2, wherein the mixing of the irradiated alkylaluminum compound with the chromium compound occurs within 3 minutes of irradiation.

4. The method of claim 1, wherein the alkylaluminum compound comprises at least one alkylaluminum compound selected from the group consisting of triethylaluminum and diethylaluminum chloride.

5. The method of claim 1, wherein the zinc compound comprises a dialkylzinc compound.

6. The method of claim 5, wherein the dialkylzinc compound comprises diethylzinc.

7. The method of claim 1, wherein the microwave radiation comprises a frequency in a range from about 0.2 GHz to about 20 GHz.

8. The method of claim 7, wherein the microwave radiation comprises a frequency of about 2.45 GHz.

9. The method of claim 1, further comprising contacting ethylene and the catalyst composition with hydrogen.

* * * * *